United States Patent
Olson et al.

(10) Patent No.: US 7,563,905 B2
(45) Date of Patent: Jul. 21, 2009

(54) TRIAZOLE DERIVATIVES AND METHOD OF USING THE SAME TO TREAT HIV INFECTIONS

(75) Inventors: Matthew Olson, Bardonia, NY (US); Martin Di Grandi, Harriman, NY (US)

(73) Assignee: Wyeth, Madison, NJ (US)

( * ) Notice: Subject to any disclaimer, the term of this patent is extended or adjusted under 35 U.S.C. 154(b) by 411 days.

(21) Appl. No.: 11/076,960

(22) Filed: Mar. 11, 2005

(65) Prior Publication Data
US 2005/0209287 A1 Sep. 22, 2005

Related U.S. Application Data

(60) Provisional application No. 60/552,810, filed on Mar. 12, 2004.

(51) Int. Cl.
*C07D 249/08* (2006.01)
(52) U.S. Cl. .................................................. 548/262.2
(58) Field of Classification Search ............... 548/262.2
See application file for complete search history.

(56) References Cited

U.S. PATENT DOCUMENTS

| | | | |
|---|---|---|---|
| 3,689,501 A | 9/1972 | Weaver et al. | 260/308 |
| 3,937,713 A | 2/1976 | Paget et al. | 260/305 |
| 4,082,762 A | 4/1978 | Paget et al. | 260/308 |
| 4,120,864 A | 10/1978 | Seidel et al. | 260/308 |
| 4,291,043 A | 9/1981 | Kristiansen et al. | 424/269 |
| 4,742,072 A | 5/1988 | Jacobson et al. | 514/384 |
| 5,223,490 A | 6/1993 | Hart et al. | 548/311 |
| 5,260,450 A | 11/1993 | Kane et al. | 424/264.4 |
| 5,496,793 A | 3/1996 | Andrea et al. | 504/273 |
| 5,508,419 A | 4/1996 | Bandurco et al. | 548/251 |
| 5,789,430 A | 8/1998 | Jautelat et al. | 514/372.2 |
| 5,859,039 A | 1/1999 | Jautelat et al. | 514/384 |
| 6,080,775 A | 6/2000 | Jautelat et al. | 514/384 |
| 6,166,059 A | 12/2000 | Jautelat et al. | 514/384 |
| 6,274,610 B1 | 8/2001 | Jautelat et al. | 514/384 |
| 6,306,959 B1 * | 10/2001 | Bolton et al. | 506/32 |
| 6,506,701 B1 * | 1/2003 | Bolton et al. | 506/15 |
| 6,525,203 B1 | 2/2003 | Tino | 548/125 |
| 6,579,892 B1 | 6/2003 | Starck et al. | 514/365 |
| 6,583,166 B1 | 6/2003 | Starck et al. | 514/384 |
| 6,894,054 B2 * | 5/2005 | Laborde et al. | 514/255.05 |
| 2003/0073726 A1 * | 4/2003 | Laborde et al. | 514/363 |

FOREIGN PATENT DOCUMENTS

| | | |
|---|---|---|
| EP | 1 293 503 A | 3/2003 |
| EP | 1 382 603 A | 1/2004 |
| WO | WO 02/64135 A | 2/2002 |
| WO | WO 03/014110 A | 2/2003 |
| WO | WO 2004/030611 A | 4/2004 |
| WO | WO 2004/050643 A | 6/2004 |
| WO | WO 2004/059012 | 7/2004 |
| WO | WO 2004/074272 A | 9/2004 |
| WO | WO 2004/079012 | 9/2004 |
| WO | WO 2004/089367 | 10/2004 |
| WO | WO 2004/089415 | 10/2004 |
| WO | WO 2005/039569 | 6/2005 |
| WO | WO 2005/072412 | 8/2005 |

OTHER PUBLICATIONS

Tetrahedron Letters, 43, 2002, 5305-5309, especially p. 5307, Figure 3.*
Telesnitsky, Blain and Goff, Methods in Enzymology, vol. 262, pp. 347-362, 1995.
Goff, Traktman and Baltimore, J. Virology, vol. 38 (I), pp. 239-248, 1981.
Graybill, Todd L. et al: "A convenient 'catch, cyclize, and release preparation of 3-thio-1,2,4-triazoles mediated by polymer-bound BEMP" Tet. Let., 43(30), pp. 5305-5309, 2002.
Muhi-Eldeen, Z. et al: "Synthesis and antimicrobial evaluation of 3-(4-tert-amino-2-butynyl) thio and alkyl/alkenylthio-4,5-disubstituted 4H-1, 2, 4-triazoles" Eur. J. Med. Chem., 26(2), pp. 237-241, 1991.
Al-Soud, Yaseen A. et al: "Synthesis antitumor and antiviral properties of some 1,2,4-triazole derivatives", IL Farmaco, 59(10), pp. 775-783, 2004.

* cited by examiner

*Primary Examiner*—Golam M. M. Shameem
*Assistant Examiner*—Susannah Chung
(74) *Attorney, Agent, or Firm*—Fitzpatrick, Cella, Harper & Scinto

(57) ABSTRACT

The present invention is directed to compounds of formula (I):

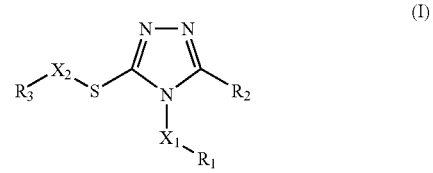

wherein $R_1$, $R_2$ and $R_3$ are independently selected from the group consisting of alkyl, alkenyl, alkynyl, cycloalkyl, aryl and heteroaryl and $X_1$ and $X_2$ are independently a bond or an linker group of 1 to 6 atoms and may be optional substituted or oxidized, or a prodrug, a pharmaceutically acceptable salt or a pharmaceutically active metabolite thereof. The invention is also directed to methods of using the same for treating HIV infections, or AIDs or preventing viral replication.

14 Claims, No Drawings

US 7,563,905 B2

TRIAZOLE DERIVATIVES AND METHOD OF USING THE SAME TO TREAT HIV INFECTIONS

This application claims the benefit of U.S. Provisional Application No. 60/552,810, filed on Mar. 12, 2004.

BACKGROUND OF THE INVENTION

1. Field of the Invention

This invention relates to triazole derivatives useful in the treatment of HIV infections and the method of their use. These compounds are useful for treating retrovirus-associated cancer, and modulating reverse transcriptase, RNase, HIV polymerase.

2. Related Background Art

The retrovirus designated human immunodeficiency virus (HIV) is the etiological agent of the complex disease that includes progressive destruction of the immune system and degeneration of the central and peripheral nervous system (acquired immune deficiency syndrome; AIDS). A common feature of retrovirus replication is reverse transcription of the RNA genome by a virally encoded reverse transcriptase. Reverse transcriptase is implicated in the infectious lifecycle of HIV, and compounds such as nucleoside and non-nucleoside reverse transcriptase inhibitors, which interfere with the function of this enzyme, have shown utility in the treatment of conditions including AIDS.

Presently, there are four categories of drugs used to treat HIV infection, which include nucleoside analogue reverse transcriptase inhibitors, non-nucleoside reverse transcriptase inhibitors and protease inhibitors. Reverse transcriptase inhibitors, including the nucleoside and non-nucleoside categories, interfere with HIV reverse transcriptase, which, as noted above, is required for viral replication. Protease inhibitors interfere with the enzyme protease, which plays a major role in viral infection. Forms of anti-HIV therapy include giving only one reverse transcriptase inhibitor at a time (monotherapy), a combination of two or more reverse transcriptase inhibitors (combination therapy), and a combination of reverse transcriptase inhibitors and protease inhibitors (combination therapy with protease inhibitors). Nucleoside analogues include AZT (zidovudine, Retrovir), ddI (didanosine, Videx), 3TC (lamivudine, Epivir), d4T (stavudine, Zerit), abacavir (Ziagen) and ddC (zalcitabine, Hivid). AZT and 3TC are also available in a single combined pill called Combivir and AZT, 3TC and abacavir are available in a single combined pill called Trizivir. Tenofovir (Viread), a nucleotide analogue, is the only nucleotide analogue currently available for prescription and is only licensed to give people on their second or later treatment combination, although it may be given to people in their first-line treatment. Nucleotide analogues are very similar to nucleoside analogues. The only difference is that nucleotide analogues, unlike nucleoside analogues, are chemically preactivated and thus require less processing in the body for them to become active. Non-nucleoside reverse transcriptase inhibitors include Sustiva, nevirapine (Viramune), and delavirdine (Rescriptor).

Many of the treatments which inhibit reverse transcriptase activity that are currently available, particularly the nucleoside analogues, are associated with serious side effects and require long term treatment to be effective. In addition, the virus is able to mutate in response to the drugs and becomes resistant to them. Therefore, there is a constant need to provide new and better treatments for HIV and AIDS and particularly new drugs that inhibit HIV reverse transcriptase.

Triazole derivatives are known for their usefulness as insecticides, fugicides, mircobicicles and plant growth regulators. Triazole compounds have also been found useful as hydrophobic textile dyes and as therapeutic agents.

In U.S. Pat. Nos. 4,742,072 and 4,291,043, it is disclosed that triazole compounds are useful as insecticides, molluscicides and plant growth regulating agents without toxicity to humans and animals.

In the following U.S. patents, triazole derivates are disclosed and their plant fugicide activity is discussed: U.S. Pat. Nos. 3,937,713, 4,082,762 and 4,120,864.

In the following U.S. patents, Triazole derivatives are shown to possess microbicide activity: U.S. Pat. Nos. 6,274, 610, 6,166,059, 6,080,775, 5,859,039, 5,789,430 and 5,496, 793.

Triazole derivatives have also been shown to be useful as therapeutic agents. In U.S. Pat. No. 5,260,450, triazole compounds are described as useful in treating muscle tension, muscle spasms, the associated pain, hyperreflexia, convulsant seizures and anxiety. Triazole compounds have been described as selective dopamine-$D_3$-receptor inhibitors useful for mediating the effects of antipyschotics and anti-Parkinson agents in U.S. Pat. Nos. 6,583,166 and 6,579,892. U.S. Pat. No. 5,508,419 discloses triazole compounds that are angiotensen II receptor antagonists, which are useful in the treatment of hypertension, congestive heart failure, elevated ocular pressure, cerebral stroke, angina, cardiac insufficiency, myocardial infraction and diabetic nephropathy.

BRIEF SUMMARY OF THE INVENTION

The present invention is directed to triazole compounds of formula (I):

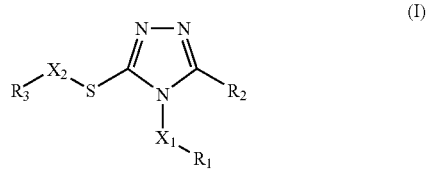

wherein:

$R_1$, $R_2$ and $R_3$ are independently selected from alkyl, alkenyl, alkynyl, cycloalkyl, aryl and heteroaryl, any of which may be optionally substituted; and $X_1$ and $X_2$ are independently a bond or a linker group, wherein said linker group consists of 1 to 6 atoms selected from of C, N, O and S, and may be optionally substituted or oxidized;

or a prodrug, a pharmaceutically acceptable salt or a pharmaceutically active metabolite thereof;

provided that $R_3$ is not a methyl or ethyl group, when $X_1$ is a bond or a methylene group, $R_1$ is a methyl or ethyl group and $R_2$ is a phenyl or naphthyl group.

The compounds of this invention are useful for inhibiting reverse transcriptase activity, polymerase activity, and RNase H activity, and more particularly, inhibiting the RNase H activity and RNA dependent DNA polymerase (RDDP) activity of HIV reverse transcriptase, and its resistant varieties, and are modulators, especially inhibitors thereof, for the treatment and prevention of HIV and AIDS. The triazole derivatives of the present invention are also useful for treating retrovirus-associated cancer, such as adenocarcinoma of the breast.

Another aspect of this invention is a method for inhibiting an HIV infection comprising administering to a mammal in need thereof an effective amount of a compound of formula (I):

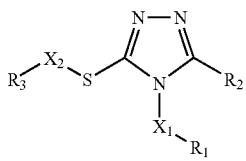

wherein $R_1, R_2, R_3, X_1$ and $X_2$ are as previously defined supra or a prodrug, a pharmaceutically acceptable salt or a pharmaceutically active metabolite thereof.

This invention is further directed toward a method for inhibiting HIV infections comprising administering to a mammal in need thereof an effective amount of a compound of formula (I):

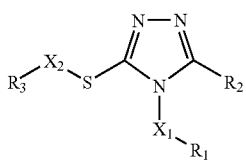

wherein $R_1, R_2, R_3, X_1$ and $X_2$ are as previously defined supra, or a prodrug, a pharmaceutically acceptable salt or a pharmaceutically active metabolite thereof, in combination with an effective amount of one or more other HIV inhibitors.

The present invention is further directed toward a method for inhibiting HIV infections comprising contacting RNase with a compound of formula (I):

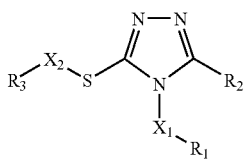

wherein $R_1, R_2, R_3, X_1$ and $X_2$ are as defined supra or a prodrug, a pharmaceutically acceptable salt or a pharmaceutically active metabolite thereof.

Another aspect of the present invention is a method directed to inhibiting HIV infections comprising contacting polymerase with a compound of formula (I):

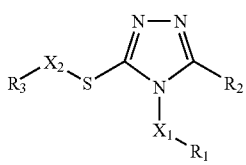

wherein $R_1, R_2, R_3, X_1$ and $X_2$ are as defined supra or a prodrug, a pharmaceutically acceptable salt or a pharmaceutically active metabolite thereof.

DETAILED DISCRIPTION

For purposes of this invention the term "alkyl" includes either straight or branched alkyl moieties. The length of a straight alkyl moiety can be from 1 to 12 carbon atoms, but is preferably 1 to 8 carbon atoms. Branched alkyl moieties can contain 3 to 12 carbon atoms, but preferably contain 3 to 8 carbon. These alkyl moieties may be unsubstituted or substituted. The term "alkenyl" refers to a substituted or unsubstitued radical aliphatic hydrocarbon containing one double bond and includes alkenyl moieties of both straight, preferably of 2 to 8 carbon atoms and branched, preferably of 3 to 8 carbon atoms. Such alkenyl moieties may exist in the E or Z configurations; the compounds of this invention include both configurations. The term "alkynyl" includes substituted and unsubstitued alkynyl moieties of both straight chain containing 2 to 8 carbon atoms and branched containing 4 to 8 carbon atoms having at least one triple bond. The term "cycloalkyl" refers to substituted or unsubstituted alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl. For purposes of this invention the term "aryl" is defined as an aromatic hydrocarbon moiety and may be substituted or unsubstituted and preferably having 6 to 12 carbon atoms. An aryl may be selected from but not limited to, the group consisting of: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups.

For purposes of this invention the term "heteroaryl" is defined as an aromatic heterocyclic ring system (monocyclic or bicyclic) and may be substituted or unsubstituted where the heteroaryl moieties are five or six membered rings containing 1 to 4 heteroatoms selected from the group consisting of S, N, and O, and include but are not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S. Preferably a heterocycle moiety contains 2 to 9 carbon atoms.

For purposes of this invention the term "heterocycloalkyl" refers to a substituted or unsubstituted alicyclic ring system (moncyclic or bicyclic) wherein the heterocycloalkyl moieties are 3 to 12 membered rings containing 1 to 6 heteroatoms selected from the group consisting of S, N, and O.

The phrase "linker group" refers a moiety of up to six atoms that connects an R group to the central ring of a compound of formula (I). The linker group is comprised of atoms selected from the group consisting of C, N, O, or S, and preferably the linker group either consists of saturated or unsaturated carbon atoms and possibly one or two heteroatoms. Most preferably the linker group is —$CH_2$— or —$CH_2CH_2$—.

For the purposes of this invention the term "oxidized" refers to the substitution of the linker group atoms with oxygen, for example a "—$CH_2$—" moiety can be oxidized to "—CHOH—" or "—C(O)—". Likewise, a "—S—" atom can be oxidized to "—SO—" or "—$SO_2$—".

For the purposes of this invention the term "alkoxy" is defined as $C_1$-$C_{12}$alkyl-O—; the term "aryloxy" is defined as aryl-O—; the term "heteroaryloxy" is defined as heteroaryl-O—; wherein alkyl, aryl, heteroaryl, are as defined above.

For purposes of this invention the term "alkylthio" is defined as $C_1$-$C_8$-alkyl-S—.

For purposes of this invention "alkoxyalkyl," denote an alkyl group as defined above that is further substituted with an alkoxy group as defined above.

For purposes of this invention "alkoxyalkoxy," denote an alkoxy group as defined above that is further substituted with an alkoxy group as defined above.

For purposes of this invention "arylthio" and "heteroarylthio," denote a thio group that is further substituted with an aryl or heteroaryl group as defined above.

The terms "monoalkylamino" and "dialkylamino" refer to moieties with one or two alkyl groups wherein the alkyl chain is 1 to 8 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1 to 8 carbon atoms.

"Acyl" is a radical of the formula —(C=O)-alkyl or —(C=O)-perfluoroalkyl wherein the alkyl radical or perfluoroalkyl radical is 1 to 8 carbon atoms; preferred examples include but are not limited to, acetyl, propionyl, butyryl, trifluoroacetyl.

The term "carbonyl" or "oxo" refers to the radical —C(O)—.

Saturated or partially saturated heteroaryl groups are defined in this invention as heterocyclic rings selected from but not limited to the moieties: azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "substituent" is used herein to refer to an atom radical, a functional group radical or a moiety radical that replaces a hydrogen radical on a molecule. Unless expressly stated otherwise, it should assumed that any of the substituents may be optionally substituted with one or more groups selected from: alkyl, halogen, haloalkyl, hydroxyalkyl, nitro, amino, hydroxy, cyano, alkylamino, dialkylamino, alkoxy, haloalkoxy, alkoxyalkyl, alkoxyalkoxy, oxo, alkylthio, mercapto, haloalkylthio, aryl, aryloxy, arylthio, heteroaryl, heteroaryloxy, heteroarylthio, acyl, —$CO_2$-alkyl, —$SO_3H$, $SO_2NH_2$, $SO_2NH$-alkyl, $SO_2NH$-$(alkyl)_2$, $CO_2H$, $CO_2NH_2$, $CO_2NH$-alkyl and $CO_2N$-$(alkyl)_2$.

For the purposes of this invention the term "substituted" refers to where a hydrogen radical on a molecule has been replaced by another atom radical, a functional group radical or a moiety radical; these radicals being generally referred to as "substituents."

In one embodiment the substituted aryl, heteroaryl, cycloalkyl, or heterocycloalkyl, may be optionally mono-, di-, tri- or tetra-substituted with substituents selected from, but not limited to, the group consisting of alkyl, acyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkylthio, —$SO_3H$, —$SO_2NH_2$, —$SO_2NH$alkyl, —$SO_2N$$(alkyl)_2$, —$CO_2H$, —$CO_2$— alkyl, $CO_2NH_2$, $CO_2NH$alkyl, and —$CO_2N(alkyl)_2$. Preferred substituents for aryl, heteroaryl, cycloalkyl, and heterocycloalkyl include but are not limited to: alkyl, halogen, amino, alkylamino, dialkylamino, trifluoromethyl, trifluoromethoxy, arylalkyl, and alkylaryl.

A preferred embodiment of this invention is where the compounds of formula (I) are defined by $R_1$, $R_2$ and $R_3$ being independently selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl and $C_2$-$C_9$ heteroaryl, any of which may be optionally substituted; $X_1$ and $X_2$ are independently a bond or a linker group, wherein said linker group consists of 1 to 6 atoms selected from the group consisting of C, N, O, and S, and can be optionally substituted or oxidized; or a prodrug, a pharmaceutically acceptable salt or a pharmaceutically active metabolite thereof.

Another preferred embodiment of the compounds of formula (I) is wherein $R_1$, $R_2$ and $R_3$ are independently selected from the group consisting of phenyl, furanyl, thiophenyl and pyridinyl, all of which may be optionally substituted and $X_1$ and $X_2$ are independently selected from the group consisting of a bond, —$CH_2$— or —$CH_2CH_2$—. More preferred is wherein $R_1$ is optionally substituted phenyl, $R_3$ is optionally substituted phenyl or pyridinyl, and $X_1$ and $X_2$ are independently a bond or —$CH_2$—, though —$CH_2$— is more preferable.

A preferred embodiment of the method of this invention is where the compounds of formula (I) are defined by $R_1$, $R_2$ and $R_3$ being independently selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl and $C_2$-$C_9$ heteroaryl, any of which may be optionally substituted; $X_1$ and $X_2$ are independently a bond or a linker group, wherein said linker group consists of 1 to 6 atoms selected from the group consisting of C, N, O, and S, and can be optionally substituted or oxidized; or a prodrug, a pharmaceutically acceptable salt or a pharmaceutically active metabolite thereof.

Another preferred embodiment of the method of this invention is where the compounds of formula (I) are defined by $R_1$, $R_2$ and $R_3$ being independently selected from the group consisting of phenyl, furanyl, thiophenyl and pyridinyl, all of which may be optionally substituted and $X_1$ and $X_2$ are independently selected from the group consisting of a bond, —$CH_2$— or —$CH_2CH_2$—. A more specific embodiment is wherein $R_1$ is optionally substituted phenyl, $R_3$ is optionally substituted phenyl or pyridinyl, and $X_1$ and $X_2$ are independently a bond or —$CH_2$—, and more preferable —$CH_2$—.

Another preferred embodiment of the method of this invention is where an effective amount of a triazole compound of the present invention is administered in combination with an effective amount of one or more other HIV inhibitors to treat mammals with HIV infections. The other HIV inhibitors may be selected from the following categories: reverse transcriptase inhibitors, non-nucleoside reverse transcriptase inhibitors and retroviral protease inhibitors. Retroviral protease inhibitors are the most preferred. It is also preferable if the other HIV inhibitor can inhibit the metabolism of other co-administered therapeutic agents. Thus, a retroviral protease inhibitor which can also inhibit cytochrome P450, such as retonavir, is preferable for combination therapy.

A preferred embodiment of the in vitro method of this invention is where the compounds of formula (I) are defined by $R_1$, $R_2$ and $R_3$ being independently selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl and $C_2$-$C_9$ heteroaryl, any of which may be optionally substituted; $X_1$ and $X_2$ are independently a bond or a linker group, wherein said linker group consists of 1 to 6 atoms selected from the group consisting of C, N, O, and S, and can be optionally substituted or oxidized; or a prodrug, a pharmaceutically acceptable salt or a pharmaceutically active metabolite thereof.

Another preferred embodiment of the in vitro method of this invention is where the compounds of formula (I) are defined by $R_1$, $R_2$ and $R_3$ being independently selected from the group consisting of phenyl, furanyl, thiophenyl and pyridinyl, all of which may be optionally substituted and $X_1$ and $X_2$ are independently selected from the group consisting of a bond, —$CH_2$— or —$CH_2CH_2$—. A more specific embodiment is wherein $R_1$ is optionally substituted phenyl, $R_3$ is optionally substituted phenyl or pyridinyl, and $X_1$ and $X_2$ are independently a bond or —$CH_2$—, and more preferable —$CH_2$—.

In a further embodiment of the invention, there is provided a method for treating or preventing retrovirus-associated cancer comprising administering to a subject an effective amount of a triazole derivative of the present invention.

The present invention also provides a method for screening for candidate triazole derivatives having RNase H and/or HIV reverse transcriptase modulatory activity.

Preferred compounds of the present invention include:
4-benzyl-3-[(4-chlorobenzyl)thio]-5-thien-2-yl-4H-1,2,4-triazole;
4-benzyl-3-(benzylthio)-5-thien-2-yl-4H-1,2,4-triazole;
4-{[(4-benzyl-5-thien-2-yl-4H-1,2,4-triazol-3-yl)thio]methyl}pyridine;
4-benzyl-3-[(4-methoxybenzyl)thio]-5-thien-2-yl-4H-1,2,4-triazole;
4-benzyl-3-(benzylthio)-5-(2-furyl)-4H-1,2,4-triazole;
4-benzyl-3-(2-furyl)-5-[(4-methoxybenzyl)thio]-4H-1,2,4-triazole;
4-benzyl-3-[(4-chlorobenzyl)thio]-5-(2-furyl)-4H-1,2,4-triazole;
2-({[4-benzyl-5-(2-furyl)-4H-1,2,4-triazol-3-yl]thio}methyl)pyridine;
3-(2-furyl)-4-(4-methoxybenzyl)-5-{[4-(trifluoromethyl)benzyl]thio}-4H-1,2,4-triazole;
4-benzyl-3-[(4-methoxybenzyl)thio]-5-phenyl-4H-1,2,4-triazole;
4-benzyl-3-(benzylthio)-5-phenyl-4H-1,2,4-triazole;
2-[4-benzyl-5-(benzylthio)-4H-1,2,4-triazol-3-yl]pyridine;
2-[4-benzyl-5-[(pyridine-4-ylmethyl)thio)-4H-1,2,4-triazole-3-yl]pyridine;
3-(2-furyl)-4-phenyl-5-{[4-(trifluoromethyl)benzyl]thio}-4H-1,2,4-triazole;
4-benzyl-3-(4-chloro-benzylsulfanyl)-5-phenyl-4H-1,2,4-triazole;
2-[4-benzyl-5-(4-methoxy-benzylsulfanyl)-4H-1,2,4-triazole-3-yl]pyridine;
2-[4-benzyl-5-(4-chloro-benzylsulfanyl)-4H-1,2,4-triazole-3-yl]pyridine; or
3-benzylsulfanyl-5-furan-2-yl-4-(4-methoxy-benzyl)-4H-1,2,4-triazole.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

The compounds of the current invention may be alkene diastereomers. The alkene diastereomers can be designated using the (E)-(Z) system. One skilled in the art will be familiar with this system of nomenclature. Where alkene compounds are disclosed without stereospecifity it is intended that both of the diastereomers are encompassed.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —$C$=$NR$, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates (mesylates), propanesulfonates, naphthalene-1-sulfonates, naphthalene-2-sulfonates, and mandelates. In the case of compounds or salts that are solids it is understood by those skilled in the art that the inventive compounds or salts may exist in different crystal forms, all of which are intended to be within the scope of the present invention and specified formulas.

An inventive compound of formula (I) or a pharmaceutically acceptable salt, prodrug, or active metabolite thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. In preferred embodiments, the inventive pharmaceutical compositions are delivered orally. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The compounds (active ingredients) may be formulated into solid oral dosage forms which may contain, but are not limited to, the following inactive ingredients: diluents (i.e., lactose, corn starch, microcrystalline cellulose), binders (i.e., povidone, hydroxypropyl methylcellulose), disintegrants (i.e., crospovidone, croscarmellose sodium), lubricants (i.e., magnesium stearate, stearic acid), and colorants (FD&C lakes or dyes). Alternatively, the compounds may be formulated into other oral dosage forms including liquids, suspensions, emulsions, or soft gelatin capsules, with each dosage form having a unique set of ingredients.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax.

When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of formula (I) or a pharmaceutically acceptable salt, prodrug, or pharmaceutically active metabolite thereof), and preferably is made up of one or more pharmaceutical dosage units. The selected dose may be administered to a mammal, for example, a human patient, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions associated with HIV infections. The amount of a given compound of the invention that will be therapeutically effective will vary depending upon factors such as the particular compound, the disease condition and the severity thereof, and the identity of the mammal in need thereof, which amount may be routinely determined by artisans.

The compounds of the present invention modulate, and preferably inhibit, RNase H nuclease activity. RNase H is an enzyme responsible for the removal of RNA primers from leading and lagging strands during DNA synthesis. It is an important enzyme for the replication of bacterial, viral and human genomes. HIV reverse transcriptase has an RNase H domain at the C-terminus of its p66 subunit. Accordingly, the compounds of the present invention modulate, and preferably inhibit, HIV reverse transcriptase. The ability of the compounds of the present invention to inhibit RNase H, and more particularly HIV reverse transcriptase, may be determined by any means known in the art.

Preferably, the RNase H/HIV reverse transcriptase modulatory activity of the compounds of the present invention may be determined by the methods described in copending U.S. Provisional Patent Application No. 60/436,125, filed Dec. 19, 2002 and PCT International Publication No. WO/2004/059012, filed Dec. 22, 2003 for ASSAY FOR RNase ACTIVITY of Olson et al., incorporated herein by reference in its entirety. Specifically, the modulatory activity of a triazole derivative of the present invention may be determined by hybridizing a target nucleic acid to a fluorescently labeled oligonucleotide probe complementary to the target nucleic acid and containing a fluorophor at one terminus and a quenching group at the other terminus to obtain a probe-target hybrid, wherein (i) the unhybridized probe adopts a conformation that places the fluorophon and quencher in such proximity that the quencher quenches the fluorescent signal of the fluorophon, and (ii) the formation of the probe-target hybrid causes sufficient separation of the fluorophon and quencher to reduce quenching of the fluorescent signal of the fluorophon. Next, a first and second sample containing the probe-target hybrid are prepared. The probe-target hybrid of the first sample is then contacted with an RNase H enzyme (such as HIV reverse transcriptase) in an amount sufficient to selectively cleave the target nucleic acid and thereby release the intact probe. The probe-target hybrid of the second sample is also contacted with the RNase H enzyme in an amount sufficient to selectively cleave the target nucleic acid and thereby release the intact probe in the presence of a triazole derivative of the present invention. The release of the probe in each sample may then be detected by measuring the decrease in the fluorescent signal of the fluorophon as compared to the signal of the probe-target hybrid. A comparison of the rate of the decrease in the fluorescent signal of the fluorophon in the two samples is made to determine whether there is a difference in the rate of the decrease in the two samples. A difference in the rate of decrease in the samples indicates that the triazole compound is a modulator of RNase H/HIV reverse transcriptase. This method is also useful to identify triazole derivatives of the present invention, wherein candidate derivatives are screened for their ability to modulate RNase/HIV reverse transcriptase activity.

The method of the present invention for modulating, and preferably inhibiting, the nuclease activity of RNase, comprises contacting RNase, either in vitro or in vivo, with the compounds of the present invention. The RNase H modulatory activity, and particularly inhibitory activity, of the compounds of the present invention indicates that they are useful for inhibiting the replication of HIV in a cell infected with HIV. It further indicates that the compounds are useful in the prevention and treatment of HIV and AIDS.

In addition, the compounds of the present invention may be useful for treating other microbial infections, including bacterial and viral infections, wherein the bacteria or virus relies on RNase H nuclease activity for replication.

The compounds may further be useful for treating certain cancers, and particularly retrovirus associated adenocarcinomas, such as breast cancer. See U.S. Pat. No. 5,223,490, incorporated herein by reference in its entirety.

The compounds of the present invention can be administered as the sole therapeutic agent or they can be administered in combination with one or more other therapeutic agents. Other useful therapeutic agents are compounds that have immunomodulating activity, antiviral or antiinfective activity and vaccines. Therapeutic agents with antiviral activity are encompassed within the following classifications: retroviral protease inhibitors (for example ritonavir, Ro-31-8959, SC-52151, KNI-227 and KNI-272), non-nucleoside reverse transcriptase inhibitors (for example Sustiva, nevirapine, delavirdine, R82193 and L-697,661) reverse transcriptase inhibitors (for example AZT, ddI, 3TC, d4T, abacavir and ddC). Ritonavir is an ideal therapeutic agent for combination therapy because besides being a potent protease inhibitor it is also known to be a potent inhibitor of cytochrome P450 monooxygenase, specifically the CYP3A, CYP2C9 and CYP2D6 isoforms. Thus, therapeutic agents administered in combination with ritonavir may experience an increase in half-life, which usually results in an increase in efficacy.

For retrovirus-associated cancer, additional anti-cancer agents may be administered. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the compounds of the present invention and other agent(s) at the same time. This may be achieved by contacting the cell with a single composition or pharmacological formulation that includes both agents, or by contacting the cell with two distinct compositions or formulations, at the same or different time, wherein one composition includes the triazole derivative and the other includes the second agent(s).

The method of the present invention for modulating, and preferably inhibiting, polymerase activity, comprises contacting polymerase, either in vitro or in vivo, with the compounds of the present invention. The polymerase modulatory activity, and particularly inhibitory activity, of the compounds of the present invention indicates that they are useful for inhibiting the replication of HIV in a cell infected with HIV. It further indicates that the compounds are useful in the prevention and treatment of HIV and AIDS.

In addition, the compounds of the present invention may be useful for treating other viral infections, wherein the virus relies on RDDP polymerase activity for replication.

The compounds may further be useful for treating certain cancers, and particularly retrovirus associated adenocarcinomas, such as breast cancer. See U.S. Pat. No. 5,223,490, incorporated herein by reference in its entirety.

Polymerase Inhibitory Activity of the Compounds of the Invention

The RNA dependent DNA polymerase (RDDP) activity of HIV RT was evaluated using polyrA-oligodT$_{12-18}$ as the template-primer allowing for TTP incorporation (Telesnitsky, A., Blain, S, and Goff, S. P. (1995) *Methods in Enzymology* 262, 347-362 and Goff, S, Traktman, P., and Baltimore, D (1981) *J. Virology* 38, 239). The Michaelis Constants for HIV RT RDDP were first determined for the two substrates TTP and polyrA-oligodT$_{12-18}$ independently. The $K_m$- values for TTP and polyrA-oligodT$_{12-18}$ were determined to be 7.1 µM and 5.4 nM, respectively.

HIV Reverse transcriptase (RT) 66/p51 at a concentration of 10800 units/mg (19.6 µM following stabilization in 50% glycerol) was obtained from Worthington. The template primer used was polyrA-oligodT12-18 at 4.47 µM as substrate was obtained from Pharmacia, as well as TTP (thymidine tri-phosphate), which was stored at a concentration of 1 mM. $^{33}$P TTP at 10 µCi/µl (3000 Ci/mmol) and 3.3 µM was obtained from NEN/DuPont. A 5× HIV RT buffer was prepared with the 1× final concentration being 50 mM Tris-HCl (pH 8.5), 6 mM MgCl$_2$, 80 mM KCl, 1 mM DTT (dithiotrheitol), 0.05% Triton X-100, 0.05 mg/ml BSA (bovine serum albumin). The wash buffer consisted of 0.5 M Na$_2$HPO$_4$ (pH 7.0). Filter plates were obtained from Millipore Corp. The scintillant used was Optiphase Supermix from Wallac/Perkin Elmer, manufactured by Fisher Chemicals.

A 25 µl reaction was generated from the reagents above in the following manner: An enzyme mix (consisting of 2.5× reaction buffer, 100% DMSO, and 25 fmol of HIV RT) and a substrate mix (consisting of 0.1625 mM TTP, 0.00725 µM $^{33}$P TTP [0.00725 µCi] and 0.015 µM polyrA-dT was generated. Both mixes were stable for up to 1 hour at room temperature. The enzyme, reverse transcriptase was added to the enzyme mix after the other constituents of the enzyme mix were made homogeneous. For the reaction, 5 µl of test compound (or 15% DMSO) was mixed with 10 µl enzyme mix and 10 µl substrate mix and the final mixture was incubated for 2 hours at room temperature. EDTA controls contained 10 fmol enzyme and was used to determine the non-specific retention of the radio-labeled nucleotide in the filter plate, i.e. it is a mock reaction. The reaction was stopped after 2 hours by the addition of 100 µl of 50 mM EDTA. The filter plates were prewashed with 200 µl of wash buffer using a vacuum applied to the filter. 100 µl of each sample was filtered through the filter plates and then they were washed 3 times with 200 µl of wash buffer. 1 microliter of reaction mix was spotted onto a filter to determine specific activity of the reaction mix. The plates were allowed to dry for 30 minutes to 60 minutes.

Scintillant was added and the counts per minute were determined in a Wallac Micro-Beta counter.

One unit of HIV RT is defined as that amount of enzyme that results in the incorporation of 1 nmol of TMP (thymidine mono-phosphate) into an acid insoluble precipitate in 10 minutes at 37° C. using polyrA oligodT$_{12-18}$ as the template primer (Worthington Enzyme Corporation Catalogue year 2001).

An enzyme mix and a substrate mix was generated. To prepare the enzyme mix, the enzyme was added to the enzyme mix last to ensure it was buffered and maintained in a reduced state (presence of dithiothreitol, DTT). It is critical not to vortex the enzyme mix after the addition of enzyme. Rather, the enzyme was mixed into solution by gentle inversion or pipetting or mixing. To generate a homogeneous mixture of the substrate solution gentle vortexing was used. The enzyme solution was added to the plates containing compounds. 5 ul of 15% DMSO was added to the non-compound containing samples. DMSO at a concentration of 3% will stimulate HIV RT RDDP activity up to 3-fold. Without the addition of DMSO in the positive control samples an underestimate of the inhibitory activity of the compound being assayed will be obtained. The enzyme was then incubated with the compound for 15 min at room temperature (~23° C.) prior to the addition of the substrate mix. The enzyme was allowed to incubate with the substrate for 2 h at room temperature (~23° C.). Under these conditions enzyme reaction was linear for >4 h and utilizes less than 7% of the available substrates (TTP and polyrA-oligodT$_{12-18}$). The assays were stopped by the addition of 100 ul of 50 mM EDTA and 100 ul of each sample was subjected to filtration in the Millipore DE MADEN OB50 plates. These plates were washed to remove unincorporated radiolabeleled nucleotides, dried and subjected to counts per minute (cpm) measurement in the Wallac Micro-Beta counter after the addition of scintillant. The quantity of TTP incorporated was then determined by the specific activity (S.A.) of the reaction mix, as discussed in the results section below, to ensure that less than 10% of the available substrates were consumed in the reaction and ensured linearity of the enzyme reaction. In addition, a mock reaction was included as a control. This reaction contained all of the assay components but contained the addition of 100 ul of 50 mM EDTA at the initiation of the reaction. This mock reaction control determined the quantity of background counts (cpm) in the reaction. IC$_{50}$-values <10 ug/ml or 10 μM were considered active (See Table II above for IC$_{50}$-values).

Calculation

The instrument used for quantitation was a Wallac Micro-Beta linked to a Windows based compatible desktop computer. The specific activity (S.A.) of the reaction mix was defined as cpm/pmol of TTP in the mix. (cpm—counts per minute in scintillation counting.) As noted above, 1 ul from a reaction was spotted in triplicate onto a filter the Millipore DE MADEN OB50 plates. This filter was not subjected to the washing procedure. It was used to accurately reflect the concentration of radioactivity per pmol of nucleotide in the reaction mixture. To determine specific activity, the following calculation was used S.A.=total cpm per ul divided by pmol TTP per ul, which provides cpm/pmol of TTP in the reaction. The K$_m$- value was ~7 μM, 6.5 μM concentration of TTP is used in the reaction.

In the reaction the incorporation of nucleotide by cpm was measured. This was converted to pmol of nucleotide incorporated by dividing the total number of cpms in the reaction by the S.A. of that reaction.

Sample Calculation

The pmol of nucleotides incorporated in reaction X was calculated as follows: Cpm of reaction X divided by a given unit of time which equals pmol of TTP incorporated in reaction X in a given unit time. The S.A. of the reaction for the HIV RT assay was: S.A.=10,000 cpm/(6.5 pmol/ul)=1538.46 cpm/pmol. The final concentration of TTP was 6.5 uM (6.5 pmol/ul). 5500 cpms were measured in reaction X, but only 100 ul of 125 ul of the reaction was transferred to the filter plate from the reaction plate. The background retention of radiolabeled nucleotide was determined to be 125 cpm (5500 cpm−125 cpm is 5375 cpm; =5375 cpm×($^{125}/_{100}$)=6718.75 cpm is the total for reaction X=6718.75 cpm/(1538.46 cpm/pmol)=4.36 pmol of TTP was incorporated. The IC$_{50}$-values for the compounds of the invention are shown in Table II above.

As reference compounds, Efavirenz was used which had an IC$_{50}$-value of <1 μM and AZT was used, which had an IC$_{50}$-value of <0.2 μM.

The general method of synthesizing the triazole derivatives of the present invention is illustrated in Scheme I.

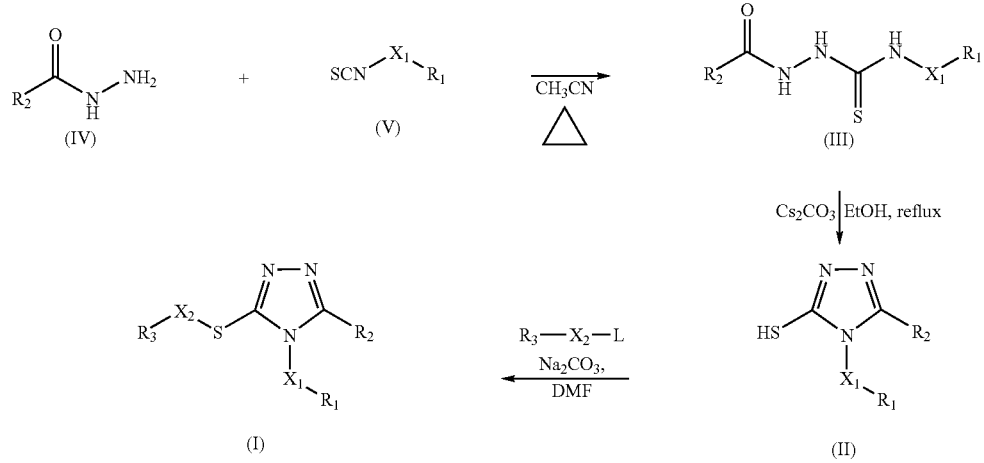

The hydrazide compound of formula (IV) and the isothiocyanate compound of formula (V) are reacted by refluxing in acetonitrile, though one skilled in the art would understand that other solvents could be used in this reaction. This provides the compound of formula (III), which is reacted under basic conditions, using $Cs_2CO_3$ and EtOH, to give the triazole compound of formula (II). This reaction can also be effected with other similar bases, such as $Na_2CO_3$, $K_2CO_3$, $Li_2CO_3$, $CaCO_3$, NaH, LiH, KH, triethylamine and pyridine. This is not an exhaustive list and other possible bases can be easily found in the technical literature. The final triazole compound of formula (I) is obtained by reacting the mercapto triazole compound of formula (II) with a base, such as $Na_2CO_3$, and a reagent of formula $R_3$—$X_2$-L, wherein L is a leaving group. Suitable leaving groups are halogens, mesylate and tosylate. The literature is replete with other possible leaving groups and one skilled in the art would be aware of these leaving groups. Sodium carbonate is not the only possible base for effecting this reaction. Other bases which can be used are $K_2CO_3$, $Li_2CO_3$, $Cs_2CO_3$, $CaCO_3$, NaH, LiH, KH, triethylamine and pyridine.

N-benzyl-2-(thien-2-ylcarbonyl)hydrazinecarbothioamide (7.5 g=26 mmol) was reacted with cesium carbonate in 95% ethanol (150 mL) at reflux and the reaction was stirred overnight. The reaction was then cooled and concentrated in vacuo. Water was added, followed by concentrated hydrochloric acid till the solution was acidic. A white solid formed and was collected by vacuum filtration, washed with water and dried in vacuo at 60° C. for 5 hours to yield 1-benzyl-2-thio-5-(2-thiophene)-1,3,4-triazole (6.4 g; 91%; $(M+H)^+$–274.4).

To a suspension of 1-benzyl-2-thio-5-(2-thiophene)-1,3,4-triazole (5.0 g=18 mmol) and 4-chlorobenzyl bromide (4.5 g=22 mmol) in N,N-dimethylformamide (25 mL) was added solid sodium carbonate (2.45 g=23 mmol) and tetrabutylammonium iodide (0.68 g=1.8 mmol). The reaction was stirred at room temperature for 2 hours where upon it was poured into water (400 mL) and the mixture was allowed to stand. A pale yellow solid formed and was collected by vacuum filtration, washed with water and air-dried. The final product was recrystallized once from acetonitrile to give the titled compound as fine white needles (5.3 g; 72%; $(M+H)^+$–399.2).

Scheme II

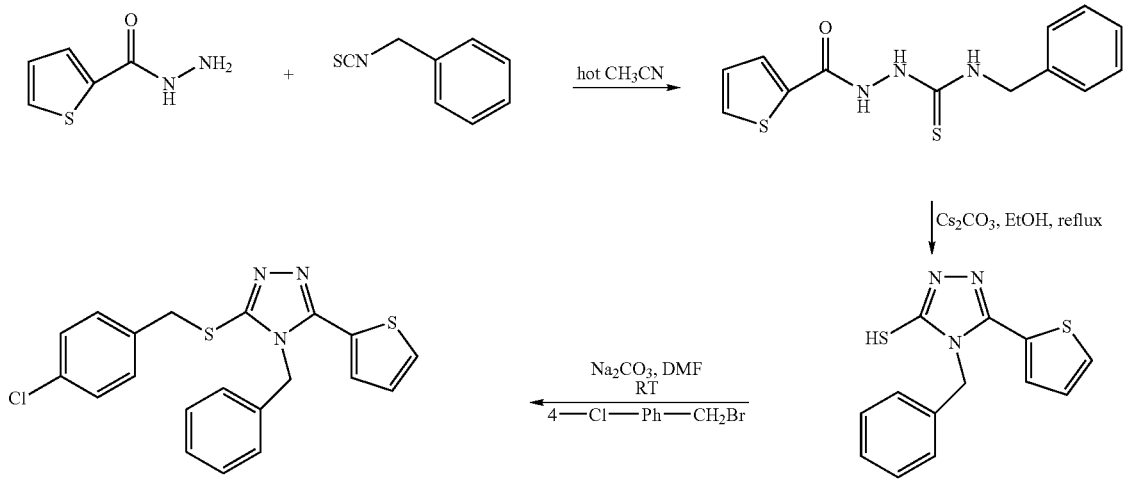

Scheme II illustrates the specific synthesis of 4-benzyl-3-[(4-chlorobenzyl)thio]-5-thien-2-yl-4H-1,2,4-triazole, Example 1. The remaining exemplified compounds were synthesized in a similar manner. These examples are provided to illustrate the invention and should not be construed as limiting the invention.

EXAMPLE 1

The Synthesis of 4-benzyl-3-[(4-chlorobenzyl)thio]-5-thien-2-yl-4H-1,2,4-triazole To a hot solution of 2-thiophencarboxylic acid hydrazide (5.0 g, 35 mmol) in acetonitrile (80 mL) was added neat benzyl isothiocyanate (4.7 mL, 35 mmol) via syringe. When the solvent started to boil, the reaction vessel was removed from the heat source and allowed to cool to room temperature. The resulting crystals were collected by vacuum filtration, washed with diethyl ether and air-dried to yield N-benzyl-2-(thien-2-ylcarbonyl)hydrazinecarbothioamide (9.11 g; 89%; $(M+H)^+$–292.2).

EXAMPLE 2

The Synthesis of 4-benzyl-3-(benzylthio)-5-thien-2-yl-4H-1,2,4-triazole

This compound was synthesized using the same methodology as described in Example 1 above, using 2-thiophencarboxylic acid hydrazide, benzyl isothiocyanate and benzyl bromide as the starting materials. (M+H)+–364.

EXAMPLE 3

The Synthesis of 4-{[(4-benzyl-5-thien-2-yl-4H-1,2,4-triazol-3-yl)thio}methyl}pyridine This compound was synthesized using the same methodology as described in Example 1 above, using 2-thiophencarboxylic acid hydrazide, benzyl isothiocyanate and 4-bromomethylpyridine as the starting materials. (M+H)+–365.

EXAMPLE 4

The Synthesis of 4-benzyl-3-[(4-methoxybenzyl) thio]-5-phenyl-4H-1,2,4-triazole

This compound was synthesized using the same methodology as described in Example 1 above, using benzoic acid hydrazide, benzyl isothiocyanate and 4-methoxybenzyl bromide as the starting materials. (M+H)+−388.

EXAMPLE 5

The Synthesis of 4-benzyl-3-(benzylthio)-5-phenyl-4H-1,2,4-triazole

This compound was synthesized using the same methodology as described in Example 1 above, using benzoic acid hydrazide, benzyl isothiocyanate and benzyl bromide as the starting materials. (M+H)+−358.

EXAMPLE 6

The Synthesis of 4-benzyl-3-(benzylthio)-5-(2-furyl)-4H-1,2,4-triazole

This compound was synthesized using the same methodology as described in Example 1 above, using 2-furancarboxylic acid hydrazide, benzyl isothiocyanate and benzyl bromide as the starting materials. (M+H)+−348.

EXAMPLE 7

The Synthesis of 2-[4-benzyl-5-(benzylthio)-4H-1,2,4-triazol-3-yl]pyridine

This compound was synthesized using the same methodology as described in Example 1 above, using 2-pyridinecarboxylic acid hydrazide, benzyl isothiocyanate and benzyl bromide as the starting materials. (M+H)+−359.

EXAMPLE 8

The Synthesis of 2-[4-benzyl-5-[(pyridine-4-ylmethyl)thio)-4H-1,2,4-triazol-3-yl]pyridine This compound was synthesized using the same methodology as described in Example 1 above, using 2-pyridinecarboxylic acid hydrazide, benzyl isothiocyanate and 4-bromomethylpyridine as the starting materials. (M+H)+−360.

EXAMPLE 9

The Synthesis of 4-benzyl-3-(2-furyl)-5-[(4-methoxybenzyl)thio]-4H-1,2,4-triazole This compound was synthesized using the same methodology as described in Example 1 above, using 2-furancarboxylic acid hydrazide, benzyl isothiocyanate and 4-methoxybenzyl bromide as the starting materials. (M+H)+−378.

EXAMPLE 10

The Synthesis of 4-benzyl-3-[(4-chlorobenzyl)thio]-5-(2-furyl)-4H-1,2,4-triazole This compound was synthesized using the same methodology as described in Example 1 above, using 2-furancarboxylic acid hydrazide, benzyl isothiocyanate and 4-chlorobenzyl bromide as the starting materials. (M+H)+−382.

EXAMPLE 11

The Synthesis of 2-({[4-benzyl-5-(2-furyl)-4H-1,2,4-triazol-3-yl]thio}methyl)pyridine This compound was synthesized using the same methodology as described in Example 1 above, using 2-furancarboxylic acid hydrazide, benzyl isothiocyanate and 4-bromomethylpyridine as the starting materials. (M+H)+−349.

EXAMPLE 12

The Synthesis of 3-(2-furyl)-4-phenyl-5-{[4-(trifluoromethyl)benzyl]thio}-4H-1,2,4-triazole This compound was synthesized using the same methodology as described in Example 1 above, using 2-furancarboxylic acid hydrazide, phenyl isothiocyanate and 4-trifluoromethylbenzyl bromide as the starting materials. (M+H)+−402.

EXAMPLE 13

The Synthesis of 4-benzyl-3-[(4-methoxybenzyl) thio]-5-thien-2-yl-4H-1,2,4-triazole This compound was synthesized using the same methodology as described in Example 1 above, using 2-thiophencarboxylic acid hydrazide, benzyl isothiocyanate and 4-methoxybenzyl bromide as the starting materials. (M+H)+−394.

EXAMPLE 14

The Synthesis of 3-(2-furyl)-4(4-methoxybenzyl)-5-{[4-(trifluoromethyl)benzyl]thio}-4H-1,2,4-triazole This compound was synthesized using the same methodology as described in Example 1 above, using 2-furancarboxylic acid hydrazide, 4-methoxybenzyl isothiocyanate and 4-trifluoromethylbenzyl bromide as the starting materials. (M+H)+−446.

EXAMPLE 15

The Synthesis of 4-benzyl-3-(4-chloro-benzylsulfanyl)-5-phenyl-4H-1,2,4-triazole This compound was synthesized using the same methodology as described in Example 1 above, using benzoic acid hydrazide, benzyl isothiocyanate and 4-chlorobenzyl bromide as the starting materials.

EXAMPLE 16

The Synthesis of 2-[4-benzyl-5-(4-methoxy-benzylsulfanyl)-4H-1,2,4-triazol-3-yl]pyridine This compound was synthesized using the same methodology as described in Example 1 above, using benzoic acid hydrazide, benzyl isothiocyanate and 4-methoxybenzyl bromide as the starting materials.

EXAMPLE 17

The Synthesis of 2-[4-benzyl-5-(4-chloro-benzylsulfanyl)-4H-1,2,4-triazol-3-yl]pyridine This compound was synthesized using the same methodology as described in Example 1 above, using 2-pyridinecarboxylic acid hydrazide, benzyl isothiocyanate and 4-chlorobenzyl bromide as the starting materials.

EXAMPLE 18

The Synthesis of 3-benzylsulfanyl-5-furan-2-yl-4-(4-methoxy-benzyl)-4H-1,2,4-triazole This compound was synthesized using the same methodology as described in Example 1 above, using 2-furancarboxylic acid hydrazide, 4-methoxybenzyl isothiocyanate and benzyl bromide as the starting materials.

The compounds of the present invention preferably inhibit RNase H and HIV reverse transcriptase with IC50 values of 1 to 100 µM. In one embodiment, the compounds of the present invention inhibit HIV reverse transcriptase with the IC50 values shown in Table I below:

TABLE I

| Example | MW | IC50(µM) |
|---|---|---|
| 1 | 398.0 | 1.3 |
| 2 | 363.5 | <0.2 |
| 3 | 364.5 | 0.2 |
| 4 | 387.5 | 1.0 |
| 5 | 357.5 | 1.0 |
| 6 | 347.4 | 1.2 |
| 7 | 358.5 | 1.7 |
| 8 | 359.5 | 2.6 |
| 9 | 377.5 | 3.8 |
| 10 | 381.9 | 3.8 |
| 11 | 348.4 | 4.0 |
| 12 | 401.4 | 4.7 |
| 13 | 393.5 | 5.9 |
| 14 | 445.5 | 6.5 |
| 15 | 391.9 | 6.0 |
| 16 | 388.5 | 7.0 |
| 17 | 392.9 | 23.0 |
| 18 | 377.5 | 46.0 |

The present invention preferably inhibit polymerase and HIV reverse with IC50 values of 1 to 300 µM. In one embodiment the compounds of the present invention inhibit the polymerase activity of HIV reverse transcriptase with the IC50 values shown in Table II

TABLE II

| Example | IC$_{50}$ |
|---|---|
| 1 | 75 |
| 2 | 27.3 |
| 3 | 11.5 |
| 4 | 103.2 |
| 5 | 4.5 |
| 6 | 12.4 |
| 7 | 30.4 |
| 8 | 21.9 |
| 9 | 56.8 |
| 10 | 57 |
| 11 | 25.2 |
| 12 | 80 |
| 13 | 103.2 |
| 14 | 100.4 |
| 15 | 100 |
| 16 | 80 |
| 17 | 80 |
| 18 | 104 |

The invention is not to be limited, except as set forth in the claims.

What is claimed:
1. A compound of formula (I):

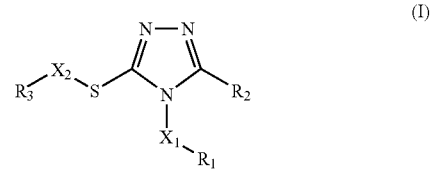

wherein:
R$_1$ is selected from aryl and heteroaryl, any of which may be optionally substituted with alkoxy, alkyl, trifluoromethyl or halo;
R$_2$ is selected from alkyl, alkenyl, alkynyl, cycloalkyl and C$_4$-C$_6$ heteroaryl, any of which may be optionally substituted with alkoxy, alkyl, trifluoromethyl or halo;
R$_3$ is selected from alkyl, alkenyl, alkynyl, cycloalkyl, aryl and heteroaryl, any of which may be optionally substituted with alkoxy, alkyl, trifluoromethyl or halo; and
X$_1$ and X$_2$ are independently a bond or a linker group, wherein said linker group consists of 1 to 6 atoms selected from C, N, O, and S and may be optionally substituted or oxidized;
or a pharmaceutically acceptable salt thereof;
provided that R$_3$ is not a methyl or ethyl group when X$_1$ is a bond or a methylene group, R$_1$ is a methyl or ethyl group and R$_2$ is a phenyl or naphthyl group.

2. The compound of claim 1, wherein:
R$_1$ and R$_3$ are independently selected from C$_6$-C$_{12}$ aryl and C$_4$-C$_6$ heteroaryl, any of which may be optionally substituted; R$_2$ is C$_4$-C$_6$ heteroaryl, which may be optionally substituted; and
X$_1$ and X$_2$ are independently a bond or a linker group, wherein said linker group consists of saturated or unsaturated carbon atoms and possible one or two hetero atoms, and can be optionally substituted or oxidized;
or a pharmaceutically acceptable salt thereof.

3. The compound of claim 2, wherein heteroaryl is selected from furyl, thienyl and pyridyl, all of which may be optionally substituted and X$_1$ and X$_2$ are independently selected from a bond, —CH$_2$— or —CH$_2$CH$_2$—;
or a pharmaceutically acceptable salt thereof.

4. The compound of claim 3, wherein R$_1$ is optionally substituted phenyl, X$_1$ is a bond or —CH$_2$— and X$_2$ is —CH$_2$—, or a pharmaceutically acceptable salt thereof.

5. The compound of claim 4, wherein R$_3$ is phenyl or pyridyl, either of which may be optionally substituted, and X$_1$ is —CH$_2$—, or a pharmaceutically acceptable salt thereof.

6. The compound of claim 5, wherein R$_2$ is optionally substituted thienyl, or a pharmaceutically acceptable salt thereof.

7. The compound of claim 6, wherein the compound is:
4-benzyl-3-[(4-chlorobenzyl)thio]-5-thien-2-yl-4H-1,2,4-triazole;
4-benzyl-3-(benzylthio)-5-thien-2-yl-4H-1,2,4-triazole;
4-{[(4-benzyl-5-thien-2-yl-4H-1,2,4-triazol-3-yl)thio]methyl}pyridine; or
4-benzyl-3-[(4-methoxybenzyl)thio]-5-thien-2-yl-4H-1,2,4-triazole;
or a pharmaceutically acceptable salt thereof.

8. The compound of claim 5, wherein $R_2$ is optional substituted furyl, or a pharmaceutically acceptable salt thereof.

9. The compound of claim 8, wherein the compound is:
4-benzyl-3-(benzylthio)-5-(2-furyl)-4H-1,2,4-triazol;
4-benzyl-3-(2-furyl)-5-[(4-methoxybenzyl)thio]-4H-1,2,4-triazole;
4-benzyl-3-[(4-chlorobenzyl)thio]-5-(2-furyl)-4H-1,2,4-triazole;
2-({[4-benzyl-5-(2-furyl)-4H-1,2,4-triazol-3-yl]thio}methyl)pyridine];
3-(2-furyl)-4(4-methoxybenzyl)-5-{[4-(trifluoromethyl)benzyl]thio}-4H-1,2,4-triazole; or
3-benzylsulfanyl-5-furan-2-yl-4-(4-methoxy-benzyl)-4H-1,2,4-triazole;
or a pharmaceutically acceptable salt thereof.

10. The compound of claim 5, wherein $R_2$ is optionally substituted pyridyl, or a pharmaceutically acceptable salt thereof.

11. The compound of claim 10, wherein the compound is:
2-[4-benzyl-5-(benzylthio)-4H-1,2,4-triazol-3-yl]pyridine;
2-[4-benzyl-5-[(pyridine-4-ylmethyl)thio)-4H-1,2,4-triazol-3-yl]pyridine;
2-[4-benzyl-5-(4-methoxy-benzylsulfanyl)-4H-1,2,4-triazol-3-yl]pyridine; or
2-[4-benzyl-5-(4-chloro-benzylsulfanyl)-4H-1,2,4-triazol-3-yl]pyridine;
or a pharmaceutically acceptable salt thereof.

12. The compound of claim 7, wherein the compound is 4-benzyl-3-[(4-chlorobenzyl)thio]-5-thien-2-yl-4H-1,2,4-triazole, or a pharmaceutically acceptable salt thereof.

13. The compound of claim 4, wherein $R_3$ is optionally substituted phenyl, $X_1$ is a bond and $R_2$ is furyl, or a pharmaceutically acceptable salt thereof.

14. The compound of claim 13, wherein the compound is 3-(2-furyl)-4-phenyl-5-{[4-(trifluoromethyl)benzyl]thio}-4H-1,2,4-triazole, or a pharmaceutically acceptable salt thereof.

* * * * *